United States Patent
Jones

[11] Patent Number: 6,015,403
[45] Date of Patent: *Jan. 18, 2000

[54] OPHTHALMIC SURGERY PROBE WITH SOFT TIP

[75] Inventor: Mark S. Jones, Ballwin, Mo.

[73] Assignee: Alcon Laboratories, Inc.

[ * ] Notice: Under 35 U.S.C. 154(b), the term of this patent shall be extended for 132 days.

[21] Appl. No.: 08/606,651

[22] Filed: Feb. 26, 1996

[51] Int. Cl.[7] ............................... A61B 17/36; A61F 9/00
[52] U.S. Cl. .................................... 606/4; 606/13
[58] Field of Search .................. 606/14, 15, 16, 606/17, 9, 4, 5, 6

[56] References Cited

U.S. PATENT DOCUMENTS

| | | | |
|---|---|---|---|
| 5,201,730 | 4/1993 | Easley et al. | 606/4 |
| 5,203,353 | 4/1993 | Easley et al. | 606/4 |
| 5,275,593 | 1/1994 | Easley et al. | 606/4 |
| 5,300,061 | 4/1994 | Easley et al. | 606/4 |
| 5,441,496 | 8/1995 | Easley et al. | 606/16 |

*Primary Examiner*—Lee Cohen
*Assistant Examiner*—Sonya Harris-Ogugua
*Attorney, Agent, or Firm*—Jeffrey S. Schira

[57] ABSTRACT

A probe for ophthalmic surgery and the like includes a handpiece terminating distally in a needle, a connector for connection to a light source such as a laser source or an illumination source, and an optical fiber for transmitting light from the light source to an eye to be treated. The optical fiber extends substantially through the handpiece needle. The needle has a soft tip to reduce the possibility of injury to the interior of the eye by contact with the metal portion of the needle. The soft tip also acts as a distance guide, allowing the user to position the optical fiber repeatedly at the same distance from the retina.

5 Claims, 3 Drawing Sheets

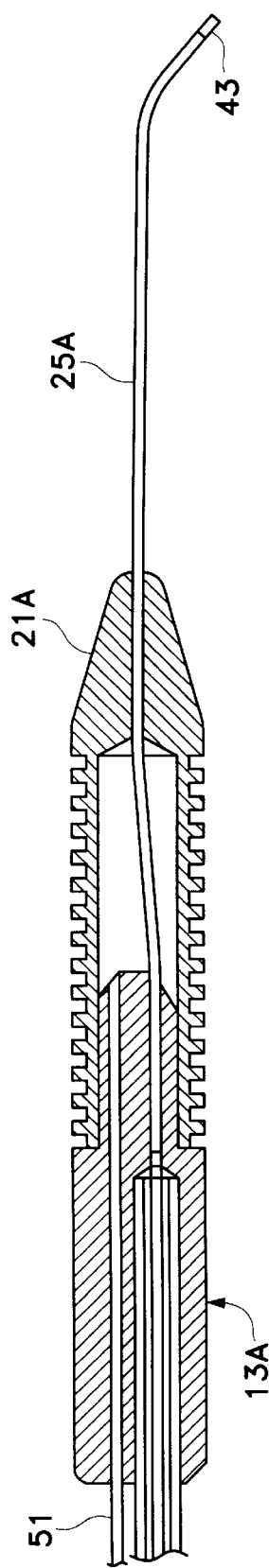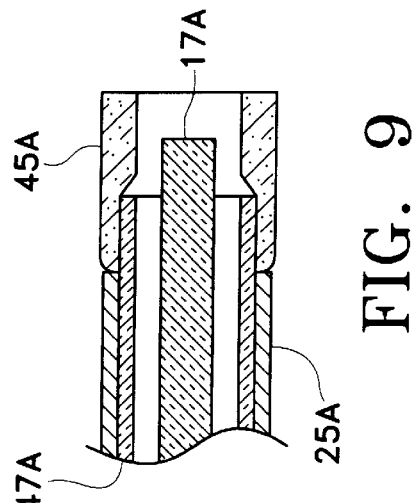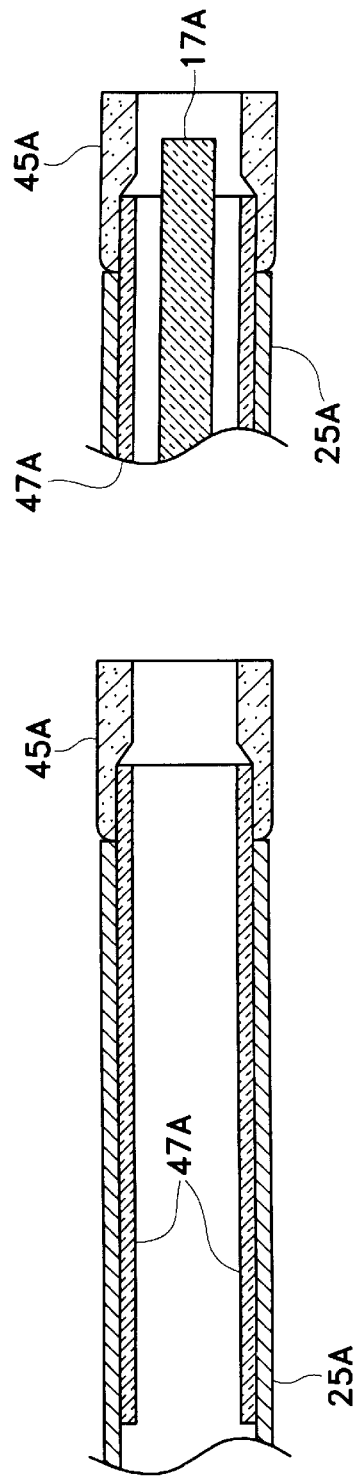

OPHTHALMIC SURGERY PROBE WITH SOFT TIP

BACKGROUND OF THE INVENTION

The present invention relates to ophthalmic probes for ophthalmic surgery and the like.

It is known that various probes may be used in ophthalmic surgery. Such probes may be used, for example, to introduce laser light from a laser source (which is disposed at some distance from the patient) through an optical fiber cable (which can be eight feet or so in length) to the patient. The optical fiber cable terminates proximally in a laser connector (for connection to the laser source) and terminates distally in a handpiece which is manipulated by the surgeon. Similarly, such probes can be used for illumination purposes when suitably connected to a source of illumination.

Although such systems perform their desired function, they could be improved. In such probes, it is known to include a suction and reflux system integral with the handpiece so that the suction could be delivered to the exact spot where necessary, and provides the surgeon the ability to manipulate the suction with the same hand with which he manipulates the laser or illumination. As a result, the surgeon does not have to remove the probe and replace it with a suction probe when suction is desired. This replacement leads to additional time for the procedure and the possibility of additional trauma, all of which is obviated by the known system.

However, the prior art system can be further improved. The eye is a fragile organ and can be easily injured. The probe, which is inserted into the eye, is generally made from stainless steel. This is, of course, a rigid material, which, if inadvertently brought into contact with various structures of the eye, such as the retina, could easily injure the eye.

SUMMARY OF THE INVENTION

Among the several objects and features of the present invention may be noted the provision of an improved ophthalmic probe which is especially suited for ophthalmic surgery or the like.

Another object is the provision of such a system which will protect the eye from accidental contact with the probe to reduce injury to the eye.

A third object is the provision of such a system which is reliable, yet relatively simple to manufacture.

Other objects and features will be in part apparent and in part pointed out hereinafter.

Briefly, an ophthalmic probe of the present invention includes a handpiece having a handpiece body and a hollow needle of a size suitable for insertion into a human eye, the hollow needle extending distally from the handpiece body and including a metal tube forming the proximal portion of the needle. A connector is provided for connection to a laser source or a source of illumination, and an optical fiber terminating at one end in the connector and terminating at another end generally at the distal end of the needle is provided for transmitting light from a light source to an eye to be treated. A soft tip is disposed at the distal end of said needle and extends distally therefrom, the soft tip being secured by molding to said needle.

In a second aspect of the present invention a method of making a probe for ophthalmic surgery includes the steps of providing a generally cylindrical, hollow bushing having a distal end, preparing the distal end to receive a molded soft tip of silicone or the like, molding the soft tip in place on the distal end of the bushing, securing the bushing with the soft tip molded thereto to a hollow probe needle such that the soft tip is disposed distally of the distal end of the probe needle, and securing the probe needle to a handpiece to form a probe.

BRIEF DESCRIPTION OF THE DRAWINGS

FIG. 7 is a sectional view, similar to FIG. 5, illustrating another embodiment of the system of FIG. 1;

FIG. 8 is a sectional view, similar to FIGS. 4 and 6, illustrating an embodiment the distal end of the ophthalmic probe of the present invention; and FIG. 9 is an enlarged view showing the relationship of the optical fiber, needle, and soft tip of the probe of FIG. 8.

Similar reference characters indicate similar parts throughout the several views of the drawings.

DESCRIPTION OF THE PREFERRED EMBODIMENTS

Figure 1:
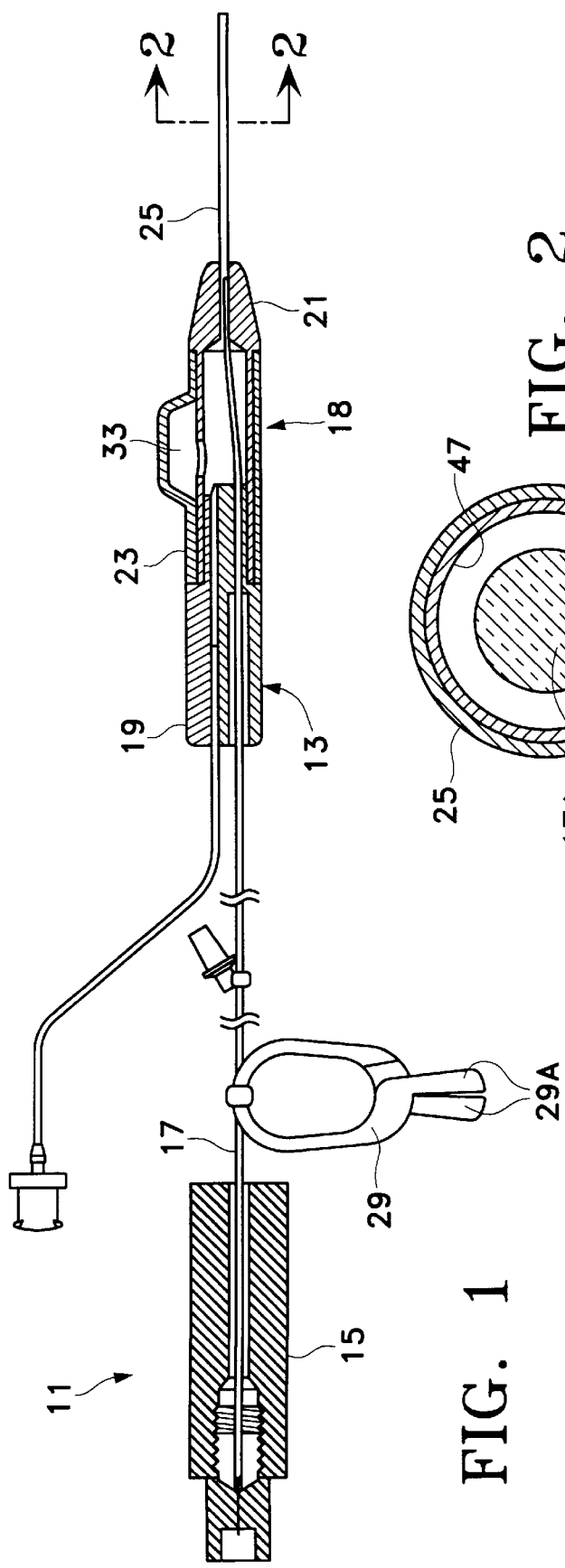
FIG. 1 is a side view, with parts broken away for clarity, of a laser delivery system.

Turning to FIG. 1, a laser delivery system 11 includes a handpiece 13 (with a distal end portion 21), a light source connector 15 (which, as is known, will vary depending upon whether the connector is designed for connection to a laser source or illumination source), and an optical fiber cable 17. Handpiece 13 has a handpiece body 18 made up of a handpiece proximal end portion 19, handpiece distal end portion 21, and a reflux sleeve 23. A hollow needle 25 of a size suitable for insertion into a human eye extends distally from the handpiece body. Needle 25 preferably includes an outer metal tube or probe needle approximately one and three-quarters inches long which is suitably secured in the distal end of the handpiece body with approximately 1.38 inches of the tube exposed distally from the handpiece body. The outer diameter of the metal tube is, for example, approximately 0.0355 inch, and its inner diameter is approximately 0.030 inch. These dimensions are illustrative of those for a tip suitable for insertion in the human eye.

Connector 15 may be of any desired construction suitable for connection to a light source (not shown). The construction shown is illustrative only.

As can be readily seen in FIG. 1, optical fiber cable 17 terminates proximally in connector 15 in such a manner that it is exposed to the light (whether laser light or illumination) from the light source. The optical cable extends for any desired length (such an eight feet or so) and terminates distally generally at the distal end of the needle 25 of handpiece 13. Optical fiber cable 17 thereby forms an optical path for the light from the light source to an eye being treated.

Also shown in FIG. 1 is a clamp 29 having jaws 29A used to removably secure cable 17 to any appropriate structure to hold the cable in place without significantly restricting movement of the handpiece by the surgeon.

Figure 2:
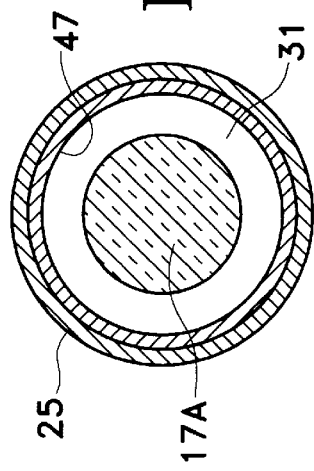
FIG. 2 is an enlarged sectional view taken along line 2—2 of FIG. 1.

Turning to FIG. 2, there is shown on a greatly enlarged scale the relationship between optical cable 17 and needle 25. The portion of optical cable 17 which is disposed in needle 25, namely an unsheathed optical fiber 17A, has an outer diameter of approximately 0.013", for example, while the inner diameter of the tip is approximately 0.020." This difference in diameter leaves a gap 31 disposed between the optical fiber and the tip. This gap runs the entire length of the tip and forms a fluid path from the distal end of needle 25 to the interior of the handpiece body.

Note that if the optical fiber were secured to needle 25 by adhesive (as has been done previously), the adhesive would tend to block off gap 31. To prevent this, the optical fiber is not secured directly to probe 25 at all. Instead it is suitably secured to proximal end portion 19 of the handpiece body. Note as well that, although the optical fiber 17 is shown centered in needle 25 in FIG. 2, the fiber can in fact be off-center in the tip without closing off gap 31.

The fluid path formed by gap 31 is in fluid communication with a cavity 33 (FIG. 1) in handpiece distal end 21. Cavity 33, in turn, is connected to a source of suction, as is known in the prior art. This allows fluid and other material to be withdrawn through the gap. Preferably, the distal end of this fluid path is disposed immediately adjacent the spot where the light exits the probe, so that removal of fluid from the operative site takes place almost exactly where needed.

Figure 3:
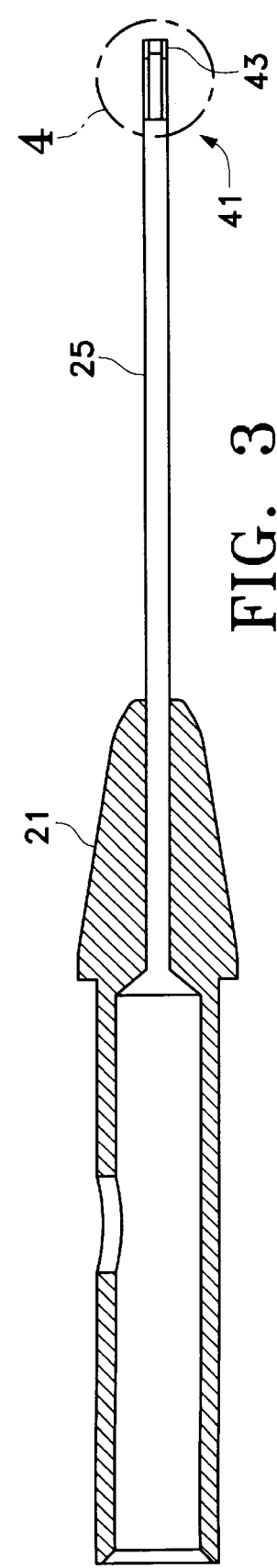
FIG. 3 is an enlarged sectional view of the distal end of a handpiece.
Figure 4:
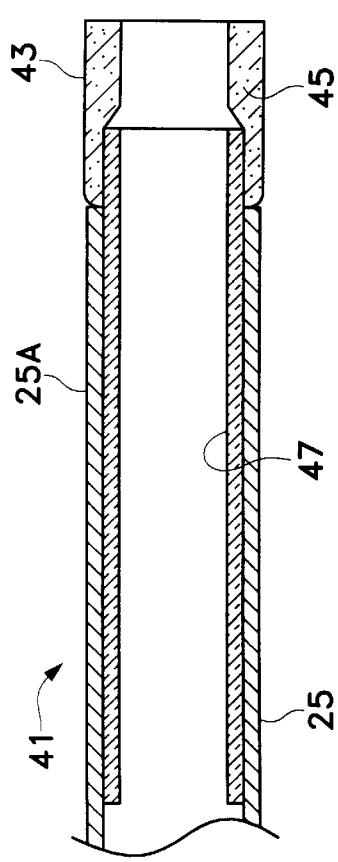
FIG. 4 is a further enlarged sectional view of the distal end of a probe of the handpiece taken along line 4—4 of FIG. 3.

The distal end 41 (see FIGS. 3 and 4) of needle 25 is provided with a tip 43 made of a soft pliable material, preferably silicone. This soft tip serves as a buffer between the structures of the eye and the metal portion of probe 25 (labeled 25A in FIG. 4), to prevent accidental injury to the eye structure caused by contact of the eye structure with the metal portion 25A of the needle, and to act as a distance guide, allowing the user to position the optical fiber repeatedly at the same distance from the retina. The tip 43 is made from a tube of silicone 45 (FIGS. 2 and 4) which is received within the needle metal portion 25A. Tube 45 is molded in place on a bushing 47 (FIGS. 2 and 4), and bushing 47 is bonded to metal portion 25A. Tube 45 extends over bushing 47 and the bushing and tube are received within metal portion 25A of needle 25. Tip 43 extends beyond the distal end of the metal portion of bushing 47 by approximately 0.030"—0.030". Tip 43 is pliable and flexible and is thus bendable. Bushing 47 extends beyond the metal portion of probe 25 by approximately 0.100" to add sufficient rigidity to tip 43 to prevent it from bending to a point where it would interfere with the beam and to provide sufficient shear strength to insure that tube 45 will not dislodge from bushing 47.

Soft tubing 45 is preferably 0.036" in outer diameter. This is approximately equal to the outer diameter of needle metal portion 25A and is greater than the 0.030" inner diameter of the metal needle portion 25A (and also greater than, or at least equal to, the 0.021" inner diameter of bushing 47). To affix tube 45 within probe metal portion 25A, the bushing 47 is bonded to metal needle portion 25A.

Figure 5:
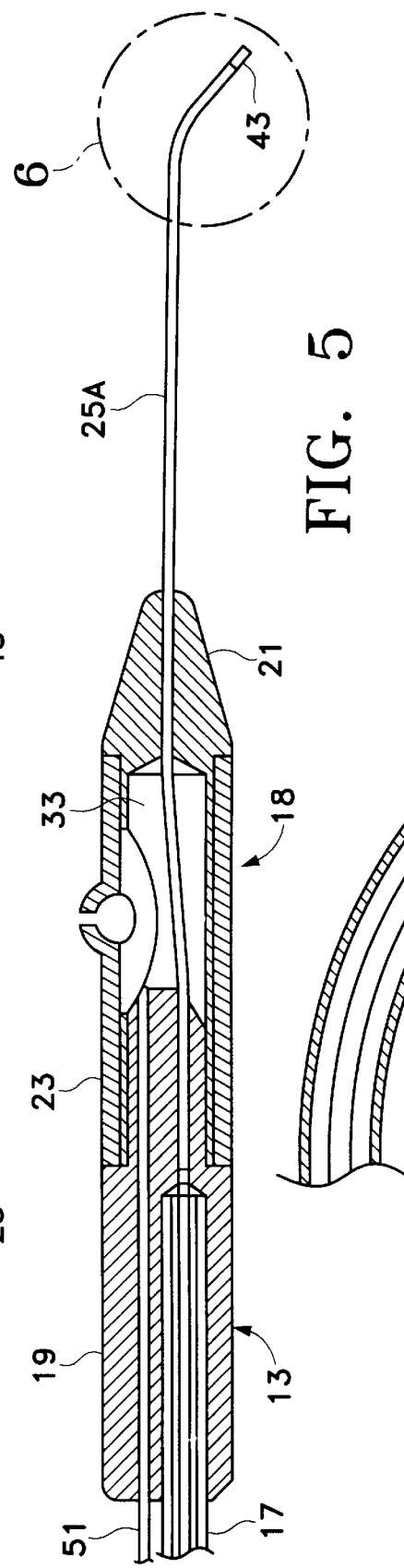
FIG. 5 is an enlarged sectional view, similar to FIG. 1, illustrating the handpiece of an alternative embodiment of the system of FIG. 1.
Figure 6:
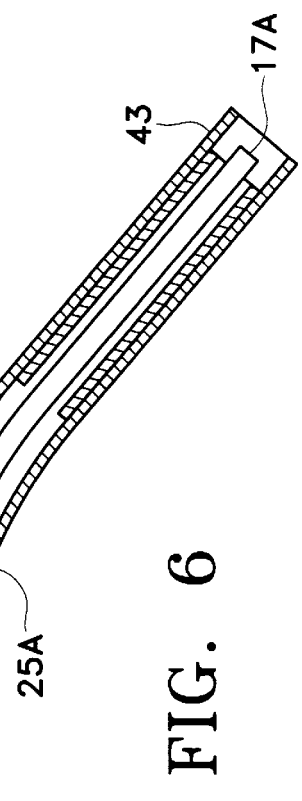
FIG. 6 is a further enlarged sectional view of the distal end of the handpiece of FIG. 5, taken along line 6—6.

Turning to FIGS. 5 and 6, a second embodiment of the present invention differs from the previous embodiment (and alternatively from the third embodiment described below) in that the distal end of the needle (labeled 25A) is curved. This enables the surgeon to access parts of the posterior segment (the interior of the eye behind the lens) that a straight needle cannot reach. Except for the curve on the end, the curved and straight needles are substantially the same so far as the present invention is concerned. The distal end of the needle is curved to form an angle (such as the 40 degree angle shown in FIG. 5) with respect to the longitudinal axis of the needle and handpiece. The needle is preferably bent starting proximal to the soft tip 43 itself (as best seen in FIG. 6). Alternatively, the bend could start at the tip itself, but that would complicate the bending process, and would not significantly improve the usability of the device by the surgeon. Although the particular radius of the curved portion of the tip can vary, depending upon the desired application, a radius of approximately ¼" was used in the device of FIGS. 5 and 6.

Turning to FIG. 7, yet another embodiment of the handpiece is shown. This handpiece, labeled 13A, differs from that of FIG. 5 mainly in that the distal portion 21A of the handpiece does not include the reflux capability of the handpieces of FIGS. 1, and 5. It has no provision for passive aspiration.

Typically, port 51 of the handpiece is connected to a syringe or a typical surgery machine that can supply suction for active aspiration. Handpiece 13A can function well without reflux because of the soft tip 43 and the type of suction used. For example, if the surgeon uses passive aspiration with the device of FIG. 1, it is possible for a membrane or part of the retina to be caught on the probe tip. Because fragile tissue caught in the hard tip of FIG. 1 will probably tear if the surgeon tries to pull the probe away, the reflux capability of the probe of FIG. 1 allows the surgeon to reflux the captured material back into the eye without damage to these fragile tissues.

When the surgeon uses passive aspiration with a probe having soft tip 43, it is doubtful whether any tissues caught in the tip would tear when the surgeon would try to pull the tip away. In that case the reflux capability of the probes shown in FIGS. 1 and 5 is not necessary. If the surgeon uses active aspiration with a probe having soft tip 43, the soft tip again reduces the possibility of tearing as the probe is pulled away. In any event, however, with active aspiration the aspiration or suction source may be used to provide reflux without the separate reflux structure shown in FIGS. 1 and 5. For these applications, the handpiece of FIG. 7 without the separate reflux structure works well, is simpler to make, and is relatively less expensive than the embodiments of FIGS. 1 and 5.

A preferred embodiment of the ophthalmic probe of the present invention is disclosed in FIGS. 8 and 9. In this embodiment, outer metal tube 25a is secured by a suitable adhesive to inner bushing 47a. Note that in this embodiment, the soft tip 45a is not captured between the outer metal tube and the bushing. Rather, the soft tip is molded in place on the bushing, and the bushing is then secured to the outer metal tube. Specifically, in this embodiment, bushing 47a is sized to fit snugly within outer metal tube 25a. The outer surface of bushing 47a is sand blasted with 75$\mu$ silica sand and a suitable primer such as the primer sold under the trade designation CF2-135 silicone primer by Nusil Technology is applied to the outer surface of the bushing as well. It is preferred that this mechanical and chemical treatment be applied to approximately the distalmost ⅒" of bushing 47a. After the outer surface of the bushing is suitably prepared, it is inserted into a suitable mold cavity (not shown) and silicone tip 45a is molded in place about the distal end of the bushing in the shape as shown in FIG. 8. A suitable material for tip 45a is the 70 durometer silicone sold under the trade designation LSR 4070 by Miles Baysilone. It has been found that this method of attachment of the soft tip to the bushing results in superior attachment characteristics. After the soft tip is molded in place, the bushing with attached soft tip is suitably glued to outer metal tube 25a to form the completed structure shown in FIG. 8. It is preferred that the gripping surface of the soft tip on the bushing extend longitudinally along the bushing for approximately 1/10". The portion of the soft tip extending distally of the bushing is preferably 0.02" or so. The bushing itself is approximately 0.23" in length, while the outer metal tube (forming the outer surface of the needle) is considerably longer.

It is preferred that the outer diameter of the soft tip be approximately the same and the outer diameter of outer metal tube 25a and that the soft tip abut the outer metal tube with only a minimal gap (i.e., 0.005") if any. The inner diameter of the soft tip is, for example, 0.022", which corresponds closely to the inner diameter of bushing 47a.

As shown in FIG. 9, once the optical fiber 17a is fixed in place, it preferably extends slightly beyond the distal end of bushing 47a, but stops proximally of the distal end of the soft tip.

In view of the above it will be seen that the various objects and features of the above described invention are achieved and other advantageous results obtained. The description and drawings of the present invention contained herein are illustrative only and are not to be interpreted in a limiting sense.

What is claimed is:

1. An ophthalmic probe for ophthalmic surgery and the like comprising:

a handpiece having a handpiece body and a hollow needle of a size suitable for insertion into a human eye, said hollow needle extending distally from the handpiece body and including a metal tube forming the proximal portion of the needle;

a connector for connection to a laser source or a source of illumination;

an optical fiber terminating at one end in the connector and terminating at another end generally at the distal end of the needle for transmitting light from a light source to an eye to be treated; and a soft tip disposed at the distal end of said needle and extending distally therefrom, said soft tip being molded in place on said needle;

said needle including an outer metal tube and an inner bushing, the inner bushing extending distally from the distal end of the outer metal tube, said inner bushing also having a proximal portion disposed inside at least a portion of the outer metal tube;

the soft tip being molded in place to the inner bushing.

2. The ophthalmic probe for ophthalmic surgery and the like as set forth in claim 1 wherein the inner bushing is fixedly secured to the outer metal tube.

3. The ophthalmic probe for ophthalmic surgery and the like as set forth in claim 1 wherein the soft tip as molded has an outer diameter approximately the same as the outer diameter of the outer metal tube.

4. The ophthalmic probe for ophthalmic surgery and the like as set forth in claim 1 wherein the proximal end of the soft tip abuts the distal end of the outer metal tube.

5. The ophthalmic probe for ophthalmic surgery and the like as set forth in claim 2 wherein the inner bushing has an outer diameter substantially equal to the inner diameter of the outer metal tube, said soft tip being solely disposed distally of the distal end of the outer metal tube.

* * * * *